Figure 1:
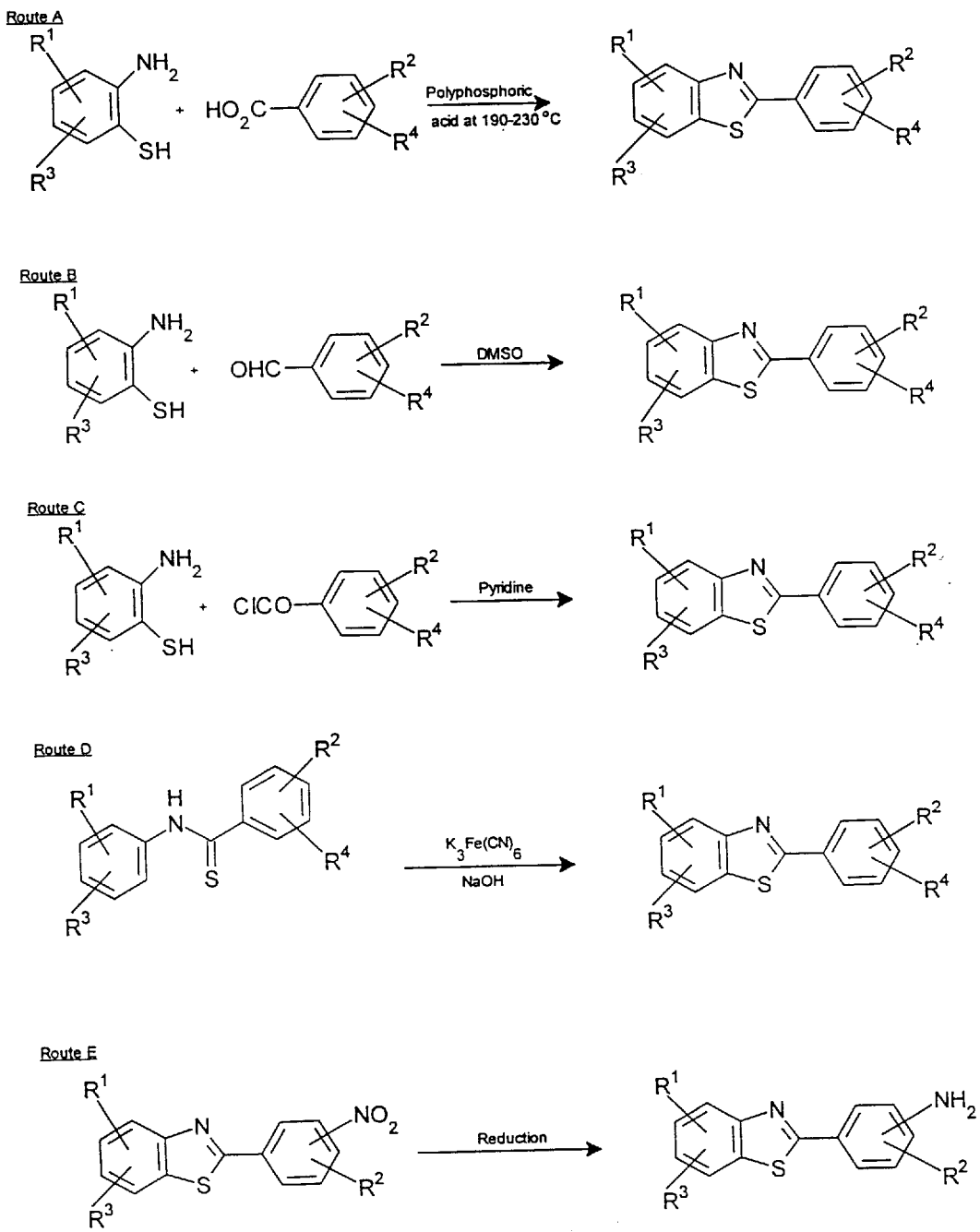

United States Patent [19]
Stevens et al.

[11] Patent Number: 5,874,431
[45] Date of Patent: Feb. 23, 1999

[54] BENZAZOLE COMPOUNDS

[75] Inventors: Malcolm F.G. Stevens, Leicestershire; Carol J. McCall, Bedfordshire, both of United Kingdom; Petrus Lelieveld, Moerkapelle, Netherlands

[73] Assignee: Cancer Research Campaign Technology Limited, Lodnon, England

[21] Appl. No.: 615,845

[22] Filed: Feb. 28, 1996

[30] Foreign Application Priority Data

Aug. 28, 1993 [GB] United Kingdom .................... 9317949
Aug. 30, 1994 [WO] WIPO ...................... PCT/GB94/01883

[51] Int. Cl.⁶ ...................... A61K 31/535; C07D 277/62; C07D 417/04
[52] U.S. Cl. ...................... 514/233.8; 546/198; 548/152; 548/178; 548/179; 514/321; 514/367
[58] Field of Search ..................................... 548/152, 178, 548/179; 544/135; 546/198; 514/233.8, 321, 367

[56] References Cited

U.S. PATENT DOCUMENTS

| | | | |
|---|---|---|---|
| 2,780,628 | 2/1957 | Porter ....................................... | 548/152 |
| 4,861,897 | 8/1989 | Press et al. .............................. | 548/217 |

FOREIGN PATENT DOCUMENTS

| | | |
|---|---|---|
| 1 255 312 | 1/1961 | France . |
| 2 684 377 | 6/1993 | France . |
| 1 080 246 | 8/1967 | United Kingdom . |
| 1 093 355 | 11/1967 | United Kingdom . |
| 2 164 648 | 3/1986 | United Kingdom . |

OTHER PUBLICATIONS

Lee, et al:"Induction of increased benzopyrene hydroxlase activity by 2–ohenylbanzothiazoles and related compounds", Chemical Abstracts, vol. 71, No. 5, Aug. 4, 1969, abstract No. 22057s, pg 323, see abstract,& Cancer Res., vol 28, No. 12, 1968, pp. 2539–2544.

Shengzhi, et al: "Crystal structures and antitumor activity of 2–(2'pyridyl)benzothiazole and its organotin complex", Chemical Abstracts, vol. 113, No. 24, Dec. 10, 1990, abstract No. 221786q, p. 661, see abstract & Inorg.Chim.Acta, vol. 173, No. 1, 1990, pp. 1–4.

Patent Abstracts of Japan, vol. 10, No. 208 (C–361), Jul. 22, 1986 & JP,A,61 105 975(Takeda Chem.Ind.Ltd) Mar. 13, 1986 see abstract.

Patent Abstracts of Japan, vol. 13, No. 402 (C–633) Sep. 6, 1989 & JP,A,01 146 875 (Kanebo Ltd) Jun 8, 1989 see abstract.

AkerfeldT: "Studies on the in vivo antiviral effects of benzothiazole derivatives against various influenza a2 strains", Journal of Medicinal Chemistry, vol. 13, No. 5, Sep. 1970, pp. 1012–1013.

Patent Abstracts of Japan, vol. 6, No. 90 (c–104), May 1982, & JP,A,57 021 375, Feb 4, 1982, see abstract.

Haskell, et al: "Neuramidinase inhibition and viral chemotherapy", Journal of Medicinal Chemistry, vol. 13, No. 4, Jul. 1970, pp. 697–704 see whole document.

Chem. Abstracts, vol. 118(23), Abst. No. 233,937f, Jun. 7, 1993

Chem. Abstracts, vol. 111(9), Abst. No. 77,907–U Aug. 28, 1989

Chem. Abstracts, vol. 106, (25), Abst. No. 213,936d Jun. 22, 1987.

Chem. Abstracts, vol. 86(1), Abst. No. 5365–h Jan. 3, 1977

(List continued on next page.)

*Primary Examiner*—Alan L. Rotman
*Attorney, Agent, or Firm*—Pillsbury Madison & Sutro LLP

[57] ABSTRACT

There are disclosed herein benzazole compounds, exemplified by 2-(4-aminophenyl)benzothiazole and analogues or salts thereof, which exhibit very significant selective cytotoxic activity in respect of tumor cells, especially breast cancer cells, and which provide potentially useful chemotherapeutic agents for treatment of breast cancer.

24 Claims, 1 Drawing Sheet

OTHER PUBLICATIONS

Chem. Abstracts, vol. 79(15), Abst. No. 92081–J Oct. 15, 1973.

Chem. Abstracts, vol. 78(21), Abst. No. 136, 153–V, May 28, 1973.

Sidgwick The Organic Chemistry of Nitrogen, pp. 140–141 Clarendon Press–Oxford Chemistry of Nitrogen, pp. 140–141 Clarendon Press–Oxford 1966 (QD 181.NI S5 1966 C–2).

BENZAZOLE COMPOUNDS

FIELD OF THE INVENTION

The present invention relates to certain biologically active benzazole compounds, particularly benzothiazole and benzoxazole compounds, which are able selectively to inhibit proliferation of certain mammalian tumour calls, particularly breast cancer cells, and which are accordingly of interest for use as active chemotherapeutic agents in antitumour therapy, especially in connection with the treatment of breast cancer.

SUMMARY OF THE INVENTION

In one aspect this invention provides, for use in therapy, 2-arylbenzazole compounds that are especially active in inhibiting proliferation of certain breast cancer tumour cells, said compounds being exemplified by 2-(4-aminophenyl) benzothiazole and close analogues or acid addition salts thereof.

More specifically, the 2-arylbenzazole compounds of the present invention are generally compounds having the structural formula I,

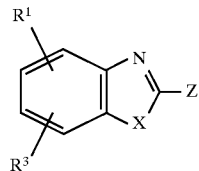

characterised in that

X is S or O;

$R^1$ and $R^3$ are each independently hydrogen, alkyl, hydroxyl, alkoxy or aralkoxy; and Z is pyridyl or is a group represented by the structural formula II below

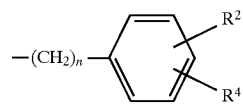

where n=0 or 1, $R^2$ is hydrogen, $NH_2$, $NO_2$, $N_3$, halogen or an alkyl or substituted alkyl oxysulphonyl group; and $R^4$ is hydrogen, $NO_2$, $N_3$, pyrrolidino, piperidino, morpholino or $NR^5R^6$ where $R^5$ and $R^6$ each represent hydrogen or alkyl;

with the proviso that when $R^4$ is hydrogen $R^2$ is selected from $NH_2$, $NO_2$ and $N_3$, and when one of $R^2$ and $R^4$ is hydrogen and the other is —$NH_2$ neither $R^1$ nor $R^3$ is 6-alkyl, and with the further proviso that alkyl groups when present as such in the compound or as a moiety in other groups such as alkoxy are each composed of less than 6 carbon atoms.

The invention also includes compounds that in use can act as precursors or prodrugs and readily break down or be converted, for example by metabolic processes, in the animal body or other biological systems so as to form the particular biologically active compounds hereinbefore specified, especially 2-arylbenzazole compounds in which the aryl group has an amino group substituent. The claims appended hereto should therefore be construed accordingly in determining the scope of the invention.

In at least most preferred embodiments of the invention wherein the benzazole compound is as specified above, at least one of $R^2$ and $R^4$ will generally be an amino or a substituted amino group, or some other nitrogen-containing group convertible into an amino group. Furthermore, usually, but not necessarily, $R^4$ will be para or in the 4-position of the phenyl group.

Particularly preferred embodiments include at least some compounds in which Z can be represented by the structural formula

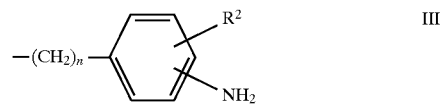

where $R^2$ is as previously defined. If $R^2$ is halogen, often it will preferably be a 2-Cl group, although in one compound hereinafter listed in accordance with the invention it is a 3-I group.

In some compounds within the scope of the invention, it is also possible for the group —$(CH_2)_n$— in the above structure II to be replaced by an alkenylic group such as —CH=CH—.

Preferred compounds of the invention in accordance with formula I wherein $R^3$ is hydrogen include compounds in which $R^1$ is alkoxy or benzyloxy, and X is preferably sulphur. More generally, preferred compounds of the invention in accordance with the structural formula I may be further characterised by at least one of the following features:

(a) at least some alkyl groups when present as such or as a moiety in other groups such as alkoxy are methyl or ethyl;

(b) halo substituents, when present, are selected from fluorine and chlorine;

(c) $R^2$ is hydrogen or 2-halogen, and $R^4$ is amino.

Compounds in accordance with the invention which conform to formula I wherein Z has the structural formula II with n=0, and which are of particular interest, include those compounds where the combination of substituents $R^1$, $R^2$, $R^3$, $R^4$ and X is selected from the following combinations:

| $R^1$ | $R^3$ | X | $R^2$ | $R^4$ |
|---|---|---|---|---|
| H | H | S | H | 4-$NH_2$ |
| H | H | S | 3-$NH_2$ | 4-H |
| H | H | S | 2-$NH_2$ | 4-H |
| H | H | S | H | 4-$NMe_2$ |
| H | H | S | H | 4-$NEt_2$ |
| H | H | S | H | 4-Pyrrolidino |
| H | H | S | H | 4-Piperidino |
| H | H | S | H | 4-Morpholino |
| H | H | S | H | 4-$NO^2$ |
| H | H | S | 3-$NO_2$ | 4-H |
| H | H | S | 2-$NO_2$ | 4-H |
| H | H | S | H | 4-$N_3$ |
| H | H | S | 3-$N_3$ | 4-H |
| H | H | S | 2-$N_3$ | 4-H |
| H | H | S | 3-I | 4-$NH_2$ |
| H | H | O | H | 4-$NH_2$ |
| H | H | O | H | 4-$N_3$ |
| H | H | S | 2-F | 4-$NH_2$ |
| H | H | S | 2-F | 4-$NO_2$ |
| H | H | S | 2-F | 4-$N_3$ |
| H | H | S | 2-Cl | 4-$NH_2$ |
| H | H | S | 2-Cl | 4-$NO_2$ |
| H | H | S | 2-Cl | 4-$N_3$ |
| 4-OMe | H | S | 2-Cl | 4-$NO_2$ |
| 5-OMe | H | S | 2-Cl | 4-$NO_2$ |
| 6-OMe | H | S | H | 4-$NO_2$ |
| 6-OMe | H | S | 2-Cl | 4-$NO_2$ |
| 7-OMe | H | S | 2-Cl | 4-$NO_2$ |

-continued

| $R^1$ | $R^3$ | X | $R^2$ | $R^4$ |
|---|---|---|---|---|
| 5-OBenzyl | H | S | 2-Cl | 4-NO$_2$ |
| 6-OBenzyl | H | S | 2-Cl | 4-NO$_2$ |
| 7-OBenzyl | H | S | 2-Cl | 4-NO$_2$ |
| 5-OMe | 6-OMe | S | H | 4-NO$_2$ |
| 6-OMe | 7-OMe | S | H | 4-NO$_2$ |
| 5-OMe | 7-OMe | S | H | 4-NO$_2$ |
| 4-OMe | H | S | 2-Cl | 4-NH$_2$ |
| 5-OMe | H | S | 2-Cl | 4-NH$_2$ |
| 6-OMe | H | S | 2-Cl | 4-NH$_2$ |
| 5-OH | H | S | 2-Cl | 4-NH$_2$ |
| 6-OH | H | S | 2-Cl | 4-NH$_2$ |
| 5-OBenzyl | H | S | 2-Cl | 4-NH$_2$ |
| H | H | S | 6-OSO$_2$CF$_3$ | 3-NH$_2$ |
| H | H | S | 3-OSO$_2$CF$_3$ | 4-NH$_2$ |
| 6-Me | H | S | 3-OSO$_2$CF$_3$ | 4-NH$_2$ |
| H | H | S | 5-OSO$_2$CF$_3$ | 2-NH$_2$ |
| 7-OBenzyl | H | S | 2-Cl | 4-NH$_2$ |
| 6-OMe | H | S | H | 4-NH$_2$ |
| 6-OH | H | S | H | 4-NH$_2$ |
| 5-OMe | 7-OMe | S | H | 4-NH$_2$ |
| 5-OH | 7-OH | S | H | 4-NH$_2$ |
| 5-OH | 7-OMe | S | H | 4-NH$_2$ |
| 5-OMe | 6-OMe | S | H | 4-NH$_2$ |

In preferred compounds, as may be apparent from the above list, $R^1$ and $R^3$ will often both be hydrogen but one or other may alternatively be alkoxy or aralkoxy, e.g. methoxy or benzyloxy, whilst at least one of $R^2$ and $R^4$ is preferably an amino or a substituted amino group (e.g.—NMe$_2$) but may alternatively be nitro, azido, hydroxy, halo, or $R^2$ and $R^4$ may collectively comprise a combination of such groups substituted at different positions. Other substitution patterns can also be of interest as will be apparent from examples herein disclosed. Although in some cases the nitro and azido substituted compounds themselves exhibit some selective cytotoxic activity, most commonly these derivatives will be used as intermediates for reduction to obtain the corresponding amino compounds. The latter are usually more likely to show a useful level of biological activity.

One especially important compound in the above list is that designated CJM 126 wherein $R^1$, $R^2$ and $R^3$ are each hydrogen, $R^4$ is 4-NH$_2$ and X is sulphur, i.e. 2-(4-aminophenyl)benzothiazole, including pharmaceutically acceptable salts thereof.

Salts of the compounds of formula I in accordance with the invention may include acid addition salts derived from an acid selected from the group comprising: hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

The invention also comprises the use of a 2-arylbenzazole compound as specified above for making a medicament or pharmaceutical composition for use in antitumour therapy, especially in the treatment of breast cancer for example.

As hereinafter described, the invention also includes pharmaceutical compositions or preparations, conveniently in unit dosage form, for use in antitumour therapy, especially breast cancer therapy, said compositions or preparations comprising as the active substance a 2-arylbenzothiazole or 2-arylbenzoxazole compound as specified above.

In general, salts of compounds such as CJM 126, e.g. hydrochloride, dihydrochloride, methanesulphonic acid and ethanesulphonic acid addition salts, should be equally effective in inhibiting proliferation of breast tumour cells insofar as such salts will dissociate in water or other aqueous media to provide the active antitumour compound. In practice these salts may be the most preferred compounds for making up acceptable pharmaceutical formulations.

Development and Testing

The invention has developed from an initial observation made when carrying out certain routine chemical investigations. During these investigations it was found that the arylbenzothiazole compound 2-(4-aminophenyl)benzothiazole, herein designated CJM 126 and sometimes referred to as ptiazammine, had a very surprising and completely unexpected high and selective activity as an anti-proliferative agent in respect of cultures of MCF-7 mammary carcinoma cells.

This is illustrated in Tables 1 and 2 at the end of the present description which show in vitro test results obtained in various sets of experiments for the cytotoxic activity of this compound CJM 126 against a range of human tumour cell lines, expressed in terms of IC$_{50}$ values (concentration or dosage required to reduce cell growth or proliferation by 50%) calculated from dose-effect curves plotted for cultures of the cells in question.

It will be seen from Table 1 that the MCF-7 cell line used in the first series of experiments was about 3000 times more sensitive to CJM 126 than other human cell lines tested. This remarkable result has been reconfirmed on several subsequent occasions, as evidenced for example by the results presented in Table 2, using fresh samples and different strains of the MCF-7 cells in later series of experiments. Thus, selective inhibition has been clearly demonstrated, for example against the following human mammary carcinoma cell lines: MCF 7-wt, MDA 468, SKBR3, ZR 75 and MDA 231 with estimated IC$_{50}$ values of about 2.9 nM, 1.6 nM, 25.9 nM, 24.7 nM, and 17.2 nM respectively. Also, a somewhat unusual biphasic dose response relationship was noted. For example, in the first series of experiments referred to above it was found that an initial decrease in cell growth for the MCF-7 cells, which gave the IC$_{50}$ value of approximately 2 ng/ml, was followed at higher doses by a small increase, and then at even greater doses there was a second decrease corresponding to an IC$_{50}$ value of about 2 $\mu$g/ml. This biphasic dose response effect has also been found to be consistently reproducible. Thus, in the later series of experiments 30 nM and 100 nM CJM 126 resulted in maximum growth inhibition of MCF-7 cells and loss of growth arrest, characterised by rising cell numbers, followed exposure to 1 $\mu$M, 3 $\mu$M and 10 $\mu$M. For MCF 7-ADR cells at low concentrations of CJM 126 growth was negligible under the experimental conditions used (seeding density 2.5×10$^2$ cells per well). However, at higher concentrations of 3 and 10 $\mu$M, CJM 126 induced proliferation of these MCF cells 7-ADR.

Although certain mammary carcinoma cell lines examined did not give a biphasic dose response following CJM 126 exposure, cell lines derived from tumours of other origins appeared generally to be insensitive to the specific inhibitory properties of CJM 126. No effect was observed, for example, on the growth of A431 cells as a result of exposure to CJM 126 over a range of concentrations (0.1 nM–10 $\mu$M). Estimated IC$_{50}$ values for some of the other cell lines tested are given in Table 2.

In other in vitro studies it was found that CJM 126 gave an IC$_{50}$ value of 2.7×10$^{-5}$M against P388 cells, and against P388R8/22 (multidrug resistant) cells it gave an IC$_{50}$ value of 5.2×10$^{-5}$M. CJM 126 was also tested against the NCI (National Cancer Institute, U.S.A.) panel of human tumour cell lines which does not contain any breast cancer cell lines, and the compound was found to be essentially non-toxic in these tests.

In carrying out the above in vitro studies, the method used for conducting the cytotoxicity assays was generally substantially as follows:

Cells were maintained in a continuous logarithmic culture in Dulbecco's medium supplemented with 10% fetal calf serum and penicillin (100 IU/ml) and streptomycin (100 μg/ml). The cells were mildly trypsinized for passage and for use in assays. On day zero, 100 μl of trypsinized tumour cells (1×10$^4$/ml) were plated in the wells of 96-well flat-bottom microtiter plates. The plates were incubated for 2 days at 37° C. and 5% CO$_2$ in air to allow the cells to adhere and resume exponential growth prior to the addition of drugs.

The compounds being tested were dissolved in a small volume of DMSO and diluted to the desired concentration with growth medium so that the final concentration of DMSO did not exceed 0.25%. On day two 50 μl of the highest drug concentration was added to the wells of column 12 and from there serially diluted 3-fold to column 1 by serial transfer of 50 μl using an 8-channel micropipette. The final volume of column 1 was adjusted to 100 μl. No additions were made to the wells of rows A and B, which served as controls. The plates were further incubated for 5 days at 37° C. and 5% CO$_2$ in air. Each compound was tested in duplicate.

On day 7 the test was terminated by the addition of 100 μl saline containing 0.002% w/v propidium iodide (Sigma), 0.3% drawing ink (Staedtler "Marsmatic 745"—Trade Mark) and 0.5% Triton X-100. The plates were kept at 4° C. overnight before reading on an inverted microscope equipped with an automated scanning stage. Fluorescence intensity was measured in arbitrary units by a photomultiplier. An HP-87 computer controlled the movement of the stage and also collected and processed the data from the multiplier.

For each compound tested a dose-response curve was obtained and the IC$_{50}$ value (the drug concentration at 50% inhibition of cell growth) was calculated.

The remarkably specific effects and activity of CJM 126 noted against human MCF-7 cells in vitro has been found subsequently to extend to in vivo tests and also to a broad range of analogues of CJM 126, as illustrated for example in Tables 3, 4 and 5.

Table 3 presents the results, including estimated IC$_{50}$ values, of cytotoxicity and proliferation or growth stimulation tests carried out in vitro for different breast cancer cell lines, including MCF7-wt, MDA 468 and MCF 7-ADR, in respect of compound CJM 126 and a range of analogues of CJM 126 identified by reference codes in the first column. The structures of these analogues will be apparent from the subsequent description herein.

The results of some of the in vivo tests carried out, and a comparison of the activity of CJM 126 with that of Mitoxantrone, are set out in Table 4. The results of similar tests carried out to evaluate the activity of CJM 126, and also of a close analogue thereof designated CJM 129, against BO (T61) human mammary carcinomas implanted in NMRI-nu/nu female mice are shown in Table 4 together with results obtained using other antitumour drugs for comparison. The results marked * are all statistically significant (p<0.05). As will be seen, CJM 126 had significant activity against MCF-7 and BO mammary tumours and there were no signs of severe toxicity following administration of a single i.p. injection of 120 mg/kg CJM 126 (Table 4). Additionally, the relative BO tumour volume was lower following daily treatment of 1 mg/kg compared with 10 or 100 mg/kg/day (Table 5).

The effect of CJM 126 (0.1, 0.01 and 0.001 mg/kg) has also been investigated in nude mice bearing human MDA 468 xenograft tumours. The biphasic response obtained in vitro following exposure of MDA 468 cultures to CJM 126 was also observed in vivo when comparable CJM 126 doses were administered. Preliminary data indicate maximum inhibition to tumour growth following daily treatment of the minimum concentration tested, as can be seen from the summary of results presented in Table 6.

Although high concentrations of CJM 126 were found actually to stimulate cell proliferation in some cases, experiments have demonstrated that a continued exposure to CJM 126 is absolutely essential to maintain this stimulation of growth effect which is observed, for example, in the 2nd phase of the MCF 7-wt response. Removal of CJM 126 led not merely to loss of proliferative potential but also to a decline in cell numbers. In contrast, it was found that cell growth following exposure to nM CJM 126 concentrations (phase 1) remained arrested after drug removal and an observed IC$_{50}$ value of 2.18 nM was not significantly affected.

In these in vitro assays, it was noted that serum factors appear to play a significant role in the 2nd phase of the CJM 126 dose response. Thus, in the presence of 1% FCS, no proliferation of colonies was observed following exposure to 3, 10, 30 μM CJM 126, and growth inhibition was maintained. Moreover, enhanced potency was detected with estimated IC$_{50}$ values in the picomolar range.

In other experiments it was established that growth of MCF 7-wt cell cultures supplemented with 1% FCS was stimulated 240%, 346% and 397% by 5, 50 and 100 ng/ml EGF respectively, but CJM 126 was able to reverse this effect and exquisitely arrest the growth of these cells. However, the dose response profiles and IC$_{50}$ values did not differ significantly from MCF 7-wt cultures supplemented by 1% FCS in the absence of EGF. It was also noted that the presence of EGF was unable to rescue the 2nd phase of the dose response, and inhibition of growth was greater than 85% for all concentrations of CJM 126 between and including 1 nM–10 μM. Similarly, in MCF 7-wt cultures supplemented with 10% FCS, the dose response to CJM 126 was not significantly altered by inclusion of EGF (5, 50 and 100 ng/ml) in experimental media.

It was also observed that CJM 126 (1 μM, 10 μM and 100 μM) showed no ability to displace iodinated EGF from EGFR. In addition, Western blot analyses utilizing an anti-phosphotyrosine primary antibody demonstrated no apparent inhibition of unstimulated or of EGF stimulated EGFR tyrosine kinase activity, and at present the mode of action of the CJM 126 compound in these biological systems is not known.

In the course of studying the in vivo activity it was found that the lethal dose value LD$_{50}$ of CJM 126, i.e. the dose that was lethal to 50% of the animals tested, was about 125 mg/kg in male DBA/2 mice when administered as a single i.p. dose. With daily administration over 3 consecutive days the LD$_{50}$ dose was >31 mg/kg/day.

Preparative Methods

In most cases the arylbenzazole compounds of the present invention can readily be synthesised by various routes from easily available starting materials, and by way of example, several such general synthetic routes, designated Route A, Route B, Route C, and Route D, are illustrated in FIG. 1 of the accompanying drawings in relation specifically to aryl-benzothiazole compounds. A reduction scheme for converting a nitro substituent of an arylbenzothiazole compound into an amino substituent is also depicted as Route E. Such nitro compounds are often prepared for use as intermediates in producing the corresponding amino compounds which usually may be expected to possess greater cytotoxic activity.

Some of the arylbenzazole compounds of the present invention are also known compounds per se that are already commercially available.

In the general method for Route A, which is also applicable to the synthesis of corresponding benzoxazole compounds, typically a mixture of the 2-aminothiophenol (0.05 Mol.) (or the 2-aminophenyl) and the appropriate benzoic acid derivative (0.05 Mol.), together with polyphosphoric acid (85 g), is heated at 190°–230° C. for 4 hours, cooled and poured into a mixture of 10% aqueous sodium bicarbonate (1000 ml) and ice. The solid product may then be collected, washed with water and recrystallized.

In the general method for Route B, typically a mixture of 2-aminothiophenol (0.05 Mol.), the appropriate benzaldehyde (0.05 Mol.) and dimethylsulphoxide (30 ml) is heated to 180° C. for 15 minutes, cooled and diluted with water (200 ml). The precipitate is then collected, washed with water and crystallised.

In the general method for Route C, assuming for example that $R^2$ is a nitro group $NO_2$, a solution of the 2-aminothiophenol (0.05 Mol.) in pyridine (50 ml) is added slowly to a mixture of the appropriate nitrobenzoyl chloride (0.05 Mol.) also in pyridine (50 ml) at 25° C. The reaction is exothermic and is cooled in an ice-bath. The mixture may then be diluted with water (200 ml) and the products are collected and washed with water.

In the general method for Route D, in a typical procedure the appropriate substituted thiobenzanilide (1 Mol. equiv.) is finely powdered and mixed with a little ethanol to form a wet paste. A 30% w/v solution of aqueous sodium hydroxide (8 Mol. equiv.) is added and diluted with water to form a suspension/solution of the thiobenzanilide in 10% w/v aqueous sodium hydroxide. Aliquots of this suspension/solution are then introduced dropwise at one minute intervals into a stirred solution of potassium ferricyanide (4 Mol. equiv.) in water at 80°–90° C. The reaction mixture is heated for a further 30 minutes, then cooled. The 2-arylbenzothiazole products are collected, washed with water and crystallised. Where $R^2$ of the 2-arylbenzothiazole compound synthesised by any of the above routes (or by any other route) is a nitro group $NO_2$, this may generally be reduced and converted into the corresponding amine as follows (Route E):

A mixture of the 2-(nitrophenyl)benzazole compound in question (0.05 Mol,) and stannous chloride dehydrate (0.25 Mol.) in absolute ethanol (200 ml) is stirred and refluxed under nitrogen for 1 to 4 hours. The ethanol is then removed under reduced pressure and the residue is dissolved in ethyl acetate (4×100 ml). The combined organic phases are next shaken with excess aqueous sodium hydroxide to liberate the free amine bases and dissolve the tin residues. The separated organic phase is washed with water, dried (magnesium sulphate) and the solvent is evaporated. Finally, the products are then crystallised.

EXAMPLES

The preparation of a number of particular compounds which are considered to be of interest for use as active therapeutic substances to inhibit proliferation of at least certain breast cancer cells and which provide examples of preferred embodiments of the invention, including CJM 126 and also analogues thereof, will now be described in more detail. The compound reference codes used in Table 3 are also quoted where applicable. It should be understood, however, that these specific examples are not intended to be construed in any way as a limitation in the scope of the invention.

Example I 2-(4-aminophenyl)benzothiazole
(Compound CJM 126)

(a) In one particular example, 2-(4-aminophenyl) benzothiazole (Compound CJM 126) was prepared in 57% yield from 2-aminothiophenol and 4-aminobenzoic acid using synthetic Route A, the final product being crystallised from methanol as pale yellow needle crystals having a melting point 155°–157° C. (aqueous solubility about 3.8 µg/ml).

(b) In another preparative example, the same compound 2-(4-aminophenyl)benzothiazole was prepared in 73% yield, as beige needles (m.p. 155°–156° C.) crystallised from methanol, by reduction with stannous chloride hydrate of 2-(4-nitrophenyl)benzothiazole. The latter was first obtained (as yellow crystals, m.p. 229°–231° C., crystallised from methanol or dimethyl formamide) either via Route C (71% yield) from 2-aminothiophenol and 4-nitrobenzoyl chloride, or via Route D (10% yield) from the corresponding thiobenzanilide and potassium ferricyanide.

Example IA

Ethanesulphonic acid salt of 2-(4-aminophenyl) benzothiazole (Compound 93003)

To prepare the ethanesulphonic acid salt, 2-(4-aminophenyl)benzothiazole (0.66 g) in ethyl acetate (100 ml) at 25° C. was treated with ethanesulphonic acid (0.338 g). The solid was collected and washed with ethyl acetate (3×50 ml) followed by diethyl ether (3×50 ml). The ethanesulphonic acid salt (0.89 g., yield 90%) had m.p. 211°–213° C.

Example IB

Dihydrochloride salt of 2-(4-aminophenyl) benzothiazole

To prepare the dihydrochloride salt, 2-(4-amino-phenyl) benzothiazole (1.5 g) was dissolved in ethyl acetate (250 ml) and a stream of dry hydrogen chloride was passed through the solution for 20 minutes. The yellow dihydrochloride salt was collected and washed with ethyl acetate followed by ether. The dihydrochloride (1.61 g) had a m.p. 267°–269° C.

Example IC 2-(4-Aminophenyl)benzothiazole methanesulphonic acid salt

To a solution of 2-(4-aminophenyl)benzothiazole (0.5 g, 2.21 mmol) in ethyl acetate (65 ml) was added dropwise methanesulphonic acid (0.215 g, 2.21 mmol) at room temperature. The reaction mixture was stirred for 30 minutes. The product was collected and washed with hot ethyl acetate to give a pale yellow powder (0.67 g, 94%), m.p. 261°–262° C.; $v_{max}$/cm$^{-1}$ 3422, 2880, 2633, 1598, 1487, 1322, 1220, 1149, 1043, 967, 780, 755, 561; $\delta_H$(DMSO-d$_6$) 8.10(1H, d, J7.9, 4-H), 8.00(3H, m, 7, 2', 6'-H), 7.52(1H, t, J7.3, 5-H), 7.42(1H, t, J7.5, 6-H), 7.06(2H, d, J8.5, 3', 5'-H), 5.72(3H, br s, NH$_{3+}$), 2.41(3H, s, CH$_3$).

In vitro assay of this compound gave IC$_{50}$ values of 0.0007 µM against MCF 7-wt cells and 0.0024 µM against MDA 468 cells, indicating a very high level of selective cytotoxic activity.

Example II 2-(2-Chloro-4-nitrophenyl)-4-methoxybenzothiazole

This compound was prepared from 2-chloro-4-nitro-2'-methoxythiobenzanilide according to the general procedure of synthetic Route D. A yellow solid formed was immediately collected by filtration when 2-chloro-4-nitro-2'-methoxythiobenzanilide was added to the solution of potassium ferricyanide. The crude product was recrystallised twice from methanol to give yellow crystals (46%), m.p. 187°–188° C.; $v_{max}$/cm$^{-1}$ 3432, 3097, 2836, 1570, 1521, 1476, 1385, 1347, 1277, 1262, 1041, 890, 773, 743; $\delta_H$(CDCl$_3$) 8.60(1H, d, J8.8, 6'-H), 8.37(1H, d, J2.3, 3'-H), 8.19(1H, dd, J2.3, 8.7, 5'-H), 7.55(1H, d, J8.1, 7-H), 7.43 (1H, t, J8.1$_1$, 6-H), 6.97(1H, d, J7.9, 5-H).

Example III

5-Benzyloxy-2-(2-chloro-4-nitrophenyl) benzothiazole

This compound was prepared from 2-chloro-4-nitro-3'-benzyloxythiobenzanilide, again according to the general procedure of synthetic Route D. The crude reaction product was separated into three fractions by flash column chromatography on silica using EtOAc-hexane-chloroform (1:6:1) as the eluate. The first fraction (52%) was 5-benzyloxy-2-(2-chloro-4-nitrophenyl)benzothiazole, m.p. 156°–157° C.; $v_{max}$/cm$^{-1}$ 3449, 1603, 1521, 1342, 1277, 1181, 1055, 829, 737; $\delta_H$ (CDCl$_3$) 8.60(1H, d, J8.8, 6'-H), 8.45(1H, d, J2.2, 3'-H), 8.27(1H, dd, J2.3, 8.8 5'-H), 7.88(1H, d, J8.9, 7-H), 7.72(1H, d, J2.4, 4-H), 7.55-7.38(5H, m, Ph-H), 7.26(1H, dd, J2.4, 8.9, 6-H), 5.23(2H, s, CH$_2$O).

Example IV 5,7-Dimethoxy-2-(4-nitrophenyl)benzothiazole

This compound was prepared from 4-nitro-3', 5'-dimethoxythiobenzanilide, also according to the general procedure of Route D. Recrystallisation from ethanol-EtOAc gave a yellow powder (60%), m.p. 238°–239° C.; $v_{max}$/cm$^{-1}$ 3442, 2949, 1605, 1579, 1528, 1428, 1352, 1312, 1155, 1126, 853, 820, 688; $\delta$H(CDCl$_3$) 8.37(2H, d, J', 5'-H), 8.26(2H, d, J9.0, 2', 6'-H), 7.24(1H, d, J2.0, 4-H), 6.58(1H, d, J2.0, 6-H), 4.01(3H, s, 7-OCH$_3$), 3.95(3H, s, 5-OCH$_3$); m/z 316(M$^{+}$), 270(M-OCH$_3$ and —CH$_3$).

Example V

6-Methoxy-2-(4-nitrophenyl)benzothiazole

This compound was prepared from 4'-methoxy-4-nitrobenzanilide, again according to the general procedure of Route D. The crude product was purified by flash column chromatography using EtOAc-hexane (1:3) as the eluate to give the title compound (62%), m.p. 216°–217° C.; $v_{max}$/cm$^{-1}$ 3448, 1593, 1518, 1342, 1315, 1265, 1219, 1066, 849; $\delta_H$ (CDCl$_3$) 8.34(2H, d, J9.1, 3', 5'-H), 8.21(2H, d, J9.1, 2',6'-H), 8.00(1H, d, J9.0, 4-H), 7.38(1H, d, J2.5, 7-H), 7.15(1H, dd, J2.6, 9.0, 5-H), 1.58(3H, s, CH$_3$), m/z 289 (M$^+$), 271(M-CH$_3$).

Example VI 2-(4-amino-2-chlorophenyl)-4-methoxybenzothiazole (Compound 93005)

This amine was obtained in 77% yield by reduction of 2-(2-Chloro-4-nitrophenyl)-4-methoxybenzothiazole according to the general procedure of synthetic Route E. Characterisation of the product was as follows: mp. 148°–150° C.; $v_{max}$/cm$^{-1}$ 3460, 3316, 3205, 2962, 1626, 1602, 1567, 1474, 1441, 1414, 1335, 1257, 1043, 772, 741; $\delta_H$(CDCl$_3$) 8.19 (1H, d, J8.6, 6'-H), 7.49 (1H, d, J8.0, 7-H), 7.31 (1H, t, J8.0, 6-H), 6.91 (d, J7.8, 5-H), 6.76 (1H, d, J2.3, 3'-H), 6.64 (1H, dd, J2.3, 8.6, 5'-H), 4.07-4.04 (5H, m, OCH$_3$, NH$_2$).

Example VII 2-(4-Amino-2-chlorophenyl)-5-benzyloxybenzothiazole (Compound DF161)

This amine was obtained by reduction of 5-benzyloxy-2-(2-chloro-4-nitrophenyl)benzothiazole, again according to the general procedure of Route E. The crude product was chromatographed on silica using EtOAc-hexane (1:1) as the eluate to give 2-(4-amino-2-chlorophenyl)-5-benzyloxybenzothiazole (90%), m.p. 119°–121° C.; $v_{max}$/cm$^{-1}$ 3456, 3380, 1629, 1599, 1443, 1260, 1171, 1051, 802; $\delta_H$(CDCl$_3$) 8.12(1H, d, J8.6, 6'-H), 7.79(1H, d, J8.7, 7-H), 7.65(1H, d, J2.4, 4-H), 7.54–7.36(5H, m, Ph-H), 7.14(1H, dd, J2.5, 8.8, 6-H), 6.81(1H, J2.3, 3'-H), 6.69(1H, dd, J2.3, 8.6, 5'-H), 5.20(2H, s, CH$_2$0), 3.77(2H, s, NH$_2$).

Example VIII 2-(4-Aminophenyl)-5,7-dimethoxybenzothiazole (Compound DF1620)

This amine was formed by reduction of 5,7-dimethoxy-2-(4-nitrophenyl)benzothiazole, also according to the general procedure of Route E. The crude product was chromatographed on silica using EtOAc-hexane (1:1) as the eluate to give 2-(4-aminophenyl)-5,7-dimethoxybenzothiazole (89%), m.p. 150°–152° C.; $v_{max}$/cm$^{-1}$ 3417, 3326, 3203, 3000, 1599, 1580, 1485, 1415, 1219, 1150, 1124, 1035, 824, 807, 631; $\delta_H$(CDCl$_3$) 7.91(2H, d, J8.6, 2', 6'-H), 7.16(1H, d, J2.0, 4-H), 7.75(2H, d, J2.0, 6-H), 4.03(2H, s, NH$_2$), 3.96(3H, s, 7-OCH$_3$), 3.91(3H, s, 5-OCH$_3$).

Example IX 2-(4-Aminophenyl)-6-methoxybenzothiazole (Compound 93002)

This amine was formed by reduction of 6-methoxy-2-(4-nitrophenyl)benzothiaxole, also according to the general procedure of Route E. The crude product was chromatographed on silica using EtOAc-hexane (1:1) as the eluate to give 2-(4-aminophenyl)-6-methoxybenzothiazole (92%), m.p. 191°–193° C.; $v_{max}$/cm$^{-1}$ 3454, 1626, 1605, 1465, 1436, 1264, 1222, 825; $\delta_H$ (DMSO-d$_6$) 7.79(1H, d, J8.9, 4-H), 7.70(2H, d, J8,6, 2',6'-H), 7.62(1H, d, J2.5, 7-H), 7.05(1H, dd, J2.6, 8.9, 5-H), 6.66(2H, d, J8.6, 3', 5'-H), 5.84(2H, s, NH$_2$), 3.84(3H, s, OCH$_3$); m/z 256 (M$^+$), 241 (M—OCH$_3$).

Example X 2-(4-Amino-2-Chlorophenyl)benzothiazole (Compound 93004)

This amine was formed by reduction of 2-(2-chloro-4-nitrophenyl)benzothiazole, again according to the general procedure of Route E. Recrystallisation from methanol gave yellow crystals (93%), m.p. 92°–94° C.; $v_{max}$/cm$^{-1}$ 3455, 3299, 3194, 1630, 1620, 1432, 1312, 1262, 1050, 847, 757, 729, 699, 626; $\delta_H$(CDCl$_3$) 8.10 (1H, d, J8.6, 6'-H), 8.04 (1H, d, J7.7, 4-H), 7.89 (1H, d, J7.9, 7-H), 7.47 (1H, dt, J1.3, 7.2, 5-H), 7.36 (1H, dt, J1.2, 7.3, 6-H), 6.78 (1H, d, J2.4, 3'-H), 6.66 (1H, dd, J2.4, 8.6, 5'-H), 4.02 (2H, s, NH2).

Example XI 2-(4-Aminophenyl)-5,7-dihydroxybenzothiazole (Compound DF162Eb)

To a stirred solution of 2-(4-aminophenyl)-5,7-dimethoxybenzothiazole (0.24 g, 0.838 mmol), obtained from Example VIII, in dry dichloromethane (15 ml) under nitrogen and at −70° C., was added dropwise boron tribromide (1.0M solution) in dichloromethane (5.9 ml) over 30 minutes. The mixture was kept stirred at −70° C. for a further 1 hour, then allowed to warm slowly to room temperature and stirred overnight. The mixture was then again cooled to −70° C. and methanol was added dropwise until no further reaction was observed. It was then poured into 8% (W/V) aqueous sodium hydroxide (50 ml). After acidification with 5M hydrochloric acid to pH7, the mixture was extracted with dichloro-methane-methanol (4:1) (3×80 ml). The combined extracts were dried (MgSO$_4$) and evaporated under reduced pressure. The crude product was then separated into two fractions by flash column chromatography on silica using EtOAc-hexane (3:2) as the eluant. The second fraction (62%) was the required 2-(4-aminophenyl)-5,7-dihydroxybenzothiazole, m.p. 294° C. (dec); $v_{max}$/cm$^{-1}$ 3438, 3342, 3216, 1603, 1482, 1456, 1434, 1295, 1159, 1093, 829; $\delta_H$ (DMSO-d$_6$) 10.30(1H, s, 7-OH), 9.43(1H, s, 5-OH), 7.70(2H, d, J8.6, 2',6'-H), 6.74(1H, d, J2.0, 4-H), 6.64(2H, d, J8.6, 3', 5'-H), 6.34(1H, d, J2.0, 6-H), 5.84(2H, s, NH$_2$).

Example XII 2-(4-Aminophenyl)-6-hydroxybenzothiazole

This compound was obtained by demethylation with boron tribromide from 2-(4-aminophenyl)-6-methoxybenzothiazole (see Example IX) in a manner similar to that described above for Example XI. The crude product was chromatographed on silica using EtOAc-hexane (1:1) as the eluate to give the title compound (89%), m.p. 262°–263° C.; $v_{max}$/cm$^{-1}$ 3487, 3388, 1620, 1460, 1289, 1238, 1175, 830; $\delta_H$ (DMSO-d$_6$) 9.71(1H, s, OH), 7.72,7.66(3H, m, 4.2',6'-H), 7.32(1H, d, J2.3, 7-H), 6.91(1H, dd, J2.4, 8.7, 5-H), 6.65(2H, d, J8.6, 3',5'-H), 5.80(2H, s, NH$_2$); m/z 242 (M$_+$).

Example XIII 2-(4-Aminophenyl)benzoxazole
(Compound DF140)

This provides an example of a benzoxazole instead of a benzothiazole. In accordance with synthetic Route A, a mixture of 2-aminophenol (1.5 g, 0.0136 mol) and 4-aminobenzoic acid (1.885 g, 0.0136 mol) in polyphosphoric acid (20 g) was heated at about 190° C. for 4 hours, then cooled and poured into 10% aqueous sodium bicarbonate (400 ml). The product was collected by filtration, washed with water and recrystallised from methanol-H$_2$O (10:1) to give small pale yellow crystals (1.76 g, 62%), m.p. 176°–178° C. (lit 185° C.); $v_{max}$/cm$^{-1}$ 3472, 3322, 3186, 1614, 1500, 1454, 1312, 1242, 1170, 1066, 830, 742; $\delta_H$(DMSO-d$_6$) 7.87(2H, d, J8.6, 2',6'-H), 7.69–7.64(2H, m, 5, 6-H), 7.36–7.28(2H, m, 4, 7-H), 6.70(2H, d, J8.6, 3', 5'-H), 6.02 (2H, s, NH$_2$).

Example XIV 2-(3-Amino-6-trifluoromethylsulphonyloxyphenyl)benzothiazole 2-(3-Azidophenyl)benzothiazole (1 g) was added in small portions (5×0.2 g) to a mixture of trifluoromethanesulphonic acid (4 ml), trifluoroacetic acid (5 ml) and triflucromethylacetic anhydride (1 ml) at 0° C. After evolution of nitrogen ceased, the mixture was stirred at 20° C. for 18 hours, basified with aqueous ammonia and the products extracted into ethyl acetate. The organic layer was washed with water, dried (MgSO$_4$) and evaporated to give a gum which was separated on silica with hexane-ethyl acetate (6:4) as eluent. The product obtained was the title compound (70% yield). (Found: M$^+$ 374. C$_{14}$H$_9$F$_3$N$_2$O$_3$S$_2$ requires MW 374). An in vitro assay of this compound against MCF-7 (wild type) cells gave an IC$_{50}$ value of 50 nM which again indicates a useful level of activity.

Example XV 2-(4-Amino-3-trifluoromethylsulphonyloxyphenyl)benzothiazole

This compound was prepared in a similar way to the compound of Example XIV from 2-(4-azidophenyl)benzothiazole. The yield was 12%, (Found: M$^+$ 374. C$_{14}$H$_9$F$_3$N$_2$O$_3$S$_2$ requires MW 374).

Example XVI 2-(4-Amino-3-trifluoromethylsulphonyloxyphenyl)-6-methylbenzothiazole This compound was prepared in a similar way to the compound of Example XIV from 2-(4-azidophenyl)-6-methyl-benzothiazole. (Found: M$^+$ 388. C$_{15}$H$_{11}$F$_3$N$_2$O$_3$S$_2$ requires MW 386).

Example XVII 2-(2-Amino-5-trifluoromethylsulphonyloxyphenyl)benzothiazole

This compound was prepared in a similar way to the compound of Example XIV from 2-(2-azidophenyl)benzothiazole (Found: M$^+$ 374. C$_{14}$H$_9$F$_3$N$_2$O$_3$S$_2$ requires MW 374).

Other analogue compounds or derivatives of interest that have been prepared using Route A comprise
2-(4-Dimethylaminophenyl)benzothiazole
2-(4-Diethylaminophenyl)benzothiazole
2-(2-Aminophenyl)benzothiazole
2-(2-Fluorophenyl)benzothiazole
2-(4-Aminobenzyl)benzothiazole
and using Route B comprise
2-(4-Hydroxyphenyl)benzothiazole
2-(4-Pyridyl)benzothiazole
2-[4-(Pyrrolidin-1-yl)phenyl]benzothiazole (Compound 93006)
and using Route C comprise
2-(3-Nitrophenyl)benzothiazole
2-(2-Chloro-4-nitrophenyl)benzothiazole
4,4'-Bis(benzothiazol-2-yl)azobenzene
and using Route D comprise
2-(2-Chloro-4-nitrophenyl)-6-methoxybenzothiazole
2-(2-Chloro-4-nitrophenyl)-7-methoxybenzothiazole
and by reduction of the corresponding nitro compound using Route E comprise
2-(3-Aminophenyl)benzothiazole (Compound CJM 129)
2-(4-Amino-2-chlorophenyl)-5-methoxybenzothiazole
2-(4-Amino-2-chlorophenyl)-6-methoxybenzothiazole
2-(4-Amino-2-chlorophenyl)-7-methoxybenzothiazole
Further analogues or derivatives of interest that have been prepared include
2-(4-Azidophenyl)benzothiazole
2-[4-(Morpholin-4-yl)phenyl]benzothiazole (Compound 93008)

2-[4-(Piperidin-1-yl)phenyl]benzothiazole (93007)
1-(Benzothiazol-2-yl)-2-(4-dimethylaminophenyl)ethene
4,4'-Bis(benzothiazol-2-yl)hydrazobenzene (Compound 126—126)
2,2'-Diamino-5,5'-Di-(benzothiazol-2-yl)biphenyl (Compound DF68D)

Commercially available analogue compounds that have been tested and considered to be of interest include 2-(4-aminophenyl)-6-methylbenzothiazole for which in vitro assays against MCF 7-wt cells gave an $IC_{50}$ value of 0.38 $\mu$M and against MDA 468 cells an $IC_{50}$ value of 0.4 $\mu$M.

It will be appreciated that some of the above listed compounds with the more complex molecular structures, for example DF68D and 126—126, may be expected to break down or to be metabolised after administration to a mammal so as to form a simpler 2-arylbenzazole compound that, in use, is the main biologically active component. Also, many of the compounds with nitrogen-containing substituents, such as azido groups and nitro groups, may similarly be converted, in use, within the body to a corresponding active amino compound.

Therapeutic Use

As already indicated, the compounds of this invention have been found to inhibit tumour cell proliferation and to have significant selective antitumour activity, especially in respect of breast cancers. Antitumour activity is evidenced for example by reduction of tumour cell number in mammals bearing breast cancer tumours and a consequent increase in survival time as compared to a control provided by animals which are untreated. Antitumour activity is further evidenced by measurable reduction in the size of solid tumours following treatment with the compounds of this invention compared to the tumours of untreated control animals.

Accordingly, as previously stated the compounds of the present invention are of particular interest for the treatment of breast cancer tumours, and the invention further provides a method for the treatment of a patient suffering from breast cancer. For this purpose, an effective non-toxic amount of the active 2-arylbenzazole compound, such as the 2-(4-aminophenyl)benzothiazole compound or an acid addition salt or close analogue thereof as hereinbefore defined, may be suitably administered, orally, parenterally (including subcutaneously, intramuscularly and intravenously), or topically. The administration will generally be carried out repetitively at intervals, for example once or several times a day.

The amount of the active compound which is required in order to be effective as an antitumour agent for treating mammals will of course vary and is ultimately at the discretion of the medical or veterinary practitioner treating the mammal in each particular case. The factors to be considered by such practitioner, e.g. a physician, include the route of administration and pharmaceutical formulation; the mammal's body weight, surface area, age and general condition; and the chemical form of the compound to be administered. However, a suitable effective antitumour dose may be in the range of about 1.0 to about 75 mg/kg bodyweight, preferably in the range of about 5 to 40 mg/kg with most suitable doses being for example in the range of 10 to 30 mg/kg. In daily treatment for example, the total daily dose may be given as a single dose, multiple doses, e.g. two to six times per day, or by intravenous infusion for any selected duration. For example, for a 75 kg mammal, the dose range could be about 75 to 500 mg per day, and it is expected that a typical dose would commonly be about 100 mg per day. If discrete multiple doses are indicated, treatment might typically be 50 mg of the arylbenzazole compound as hereinbefore defined, given 4 times per day in the form of a tablet, capsule, liquid (e.g. syrup) or injection. On account of the biphasic dose response characteristics of many of these compounds, however, care should be taken, particularly in the initial stages of treatment, to ensure that dosage amounts are not too high.

While it may be possible for the active compound of this invention to be administered alone as the raw chemical, it is preferable to present the active compound as a pharmaceutical formulation. Formulations of the present invention, for medical use, comprise the active compound together with one or more pharmaceutically acceptable carriers thereof and, optionally, any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising an arylbenzazole compound as hereinbefore specified (possibly in the form of a free-base or a pharmaceutically acceptable acid addition salt) together with a pharmaceutically acceptable carrier thereof.

The formulations include those suitable for oral, rectal, topical and parenteral (including subcutaneous, intramuscular and intravenous) administration.

The formulations may conveniently be presented in unit dosage form and may be prepared by any of the methods well known in the art of pharmacy. All methods include generally the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parental administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

From another aspect, the invention thus also comprises use of a benzazole compound as hereinbefore specified for the manufacture of a medical preparation for the treatment of breast cancer tumours.

TABLE 1

In Vitro cytotoxicity of CJM 126 against human cell lines (1st series of experiments)

| Cell Line | | $IC_{50}$(ng/ml) |
|---|---|---|
| MCF-7 | mammary carcinoma | 2 |
| A2O4 | rhabdomyosarcoma | 5943 |
| T24 | bladder carcinoma | 16876 |
| WiDr | colon carcinoma | 6008 |
| IGR37 | melanoma | 23986 |
| HT29 | colon carcinoma | 7568 |
| A2780 | ovarian carcinoma | 8826 |

TABLE 2

$IC_{50}$ values for CJM 126 against human cell lines (2nd series of experiments)

| Cell Line | $IC_{50}$ $\mu M$ |
|---|---|
| MCF 7 mammary (ER+) | 0.003 |
| MCF 7 mammary (ER+) | 0.008 |
| MCF 7-ADR mammary | stimulation > 1 $\mu M$ |
| ZR 75 mammary (ER+) | 0.028 |
| SKBR mammary (ER−) | 0.026 |
| MDA 468 mammary (ER−/EGFR+) | 0.0016 |
| MDA 231 mammary (EGFR+/erbB3+) | .017 |
| T47D mammary (ER−) | 44.1 |
| MCF 7-B (ER+) | 62.2 |
| MCF 7-T (ER−) | 12.87 |
| A204 rhabdomyosarcoma | 26 |
| T24 bladder carcinoma | 75 |
| WiDr colon | 26 |
| IGR 37 melanoma | 106 |
| HT 29 colon | 33 |
| A2780 ovarian carcinoma | 39 |
| A2780 ovarian carcinoma | 43 |
| A2780/CisR | 37 |
| HX/62 ovarian carcinoma | 120 |
| SKOV-3 ovarian carcinoma | 64 |
| 41M ovarian carcinoma | 36 |
| 41M/CisP | 40 |
| CH 1 ovarian carcinoma | 22 |
| CH 1/CisR | 33 |

TABLE 3

Cytotoxicity ($IC_{50}$) and growth stimulation of analogues of CJM 126 in breast cancer cell lines in vitro

| | MCF-wt ($\mu M$) | | MDA 468 ($\mu M$) | | MCF7-Adr ($\mu M$) | | |
|---|---|---|---|---|---|---|---|
| Compound | A | B | A | B | A | B | C |
| CJM126 | 0.003 | — | 0.0016 | — | — | — | >1 |
| DF140 | 0.11 | — | — | >10 | — | — | 10, 30 |
| DF161 | 0.001 | 55.9 | 0.0007 | 2.84 | — | 84.8 | 3, 10, 30 |
| 93002 | 0.38 | — | — | 7.64 | — | — | 3, 10 |
| 93003 | 0.0046 | — | 0.0024 | — | — | — | 3, 10 |
| 93004 | 0.142 | — | 0.003 | — | — | — | 1, 3, 10 |
| CJM129 | — | >10 | NT | NT | Inactive | | |
| DF126-126 | — | >10 | NT | NT | Inactive | | |
| 93005 | 0.063 | — | 0.0022 | NT | 0.0465 | — | 3, 10 |
| 93006 | 0.867 | — | NT | NT | — | — | 3, 10 |
| 93007 | — | 2.77 | NT | NT | — | — | 1, 3, 10 |
| 93008 | 0.160 | — | NT | NT | — | — | 3, 10 |
| DF162Eb | — | 49.65 | — | 16.3 | — | 13.9 | — |
| DF162D | — | 19.3 | 0.0035 | — | — | 20.9 | — |
| DF68D | — | 22.3 | — | 19.3 | Inactive | | |

A $IC_{50}$ at sub-micromolar concentrations
B $IC_{50}$ at > micromolar concentrations
C Concentrations which stimulate cell growth
NT Not tested

TABLE 4

In vivo activity of CJM 126 against MCF-7 mammary carcinoma

| | | | | Relative tumour volume (T/C %) | | | | | |
|---|---|---|---|---|---|---|---|---|---|
| Compound | Route | Dose mg/kg/day | BWC (%) | d9 | d13 | d20 | d27 | d35 | d43 |
| CJM 126 | i.p. | 120 | −13 | 84 | 47* | 38* | 27* | 27* | 43* |
| Mitoxantrone | i.v. | 10 | −10 | 52 | 32* | 38* | 26* | 29* | 29* |

Mice: Bln. NMRI - nu/nu (female)
Tumour: MCF-7 implanted s.c. supplemented with oestradiol
Treatment schedule: qd 6, 13, 20 by indicated route.
BWC: Body weight change relative to saline treated animals
Control: Saline
*Statistically significant (p < 0.05)

TABLE 5

In vivo activity of CJM 126 and CJM 129 against BO mammary carcinoma

| Compound | Route | Dose (mg/kg/day) | BWC | \multicolumn{5}{c}{Relative tumour volume (T/C %)} | | | | |
|---|---|---|---|---|---|---|---|---|
| | | | | d33 | d41 | d47 | d55 | d61 |
| CJM 126 | i.p. | 100 | −7 | 137 | 77 | 87 | 68 | 52 |
| CJM 126 | i.p. | 10 | −4 | 107 | 74 | 55 | 70 | 52 |
| CJM 126 | i.p. | 1 | −5 | 173 | 72 | 25* | 67 | 41* |
| CJM 129 | i.p. | 200 | −6 | 78* | 45* | 32* | 33* | 36* |
| CJM 129 | i.p. | 20 | −3 | 88 | 77 | 54 | 73 | 48* |
| CJM 129 | i.p. | 2 | 2 | 127 | 91 | 94 | 95 | 78 |
| Vincristine | i.p. | 1 | −6 | 142 | 62 | 61 | 61 | 57 |
| Cyclophosphamide | i.p. | 150 | −4 | 117 | 27* | 29* | 19* | 5* |
| Mitoxantrone | i.v. | 10 | −5 | 58* | 26* | 6* | 7* | 4* |

Treatment schedule: for CJM 126 and CJM 129 qd 27, 34, 41; for vincristine, cyclophosphamide and mitoxantrone qd 27.
CJM 129 is 2-(3-aminophenyl)benzothiazole
For other details: see footnotes to Table 4

TABLE 6

Activity of CJM 126 against human MDA 468 tumour in vivo.

| Day | Control | .001 mg/kg | .01 mg/kg | 0.1 mg/kg |
|---|---|---|---|---|
| | \multicolumn{4}{c}{Cross section tumour area (mm) Group} | | | |
| 5 | 95.28 + 4.61 | 85.54 + 19.44 | 120.78 + 5.83 | 97.75 + 9.55 |
| 12 | 62.88 + 8.10 | 52.93 + 2.65 | 71.65 + 11.67 | 71.07 + 7.2 |
| 15 | 86.02 + 8.65 | 67.81 + 12.92 | 78.21 + 6.69 | 82.17 + 10.58 |
| 19 | 118.35 + 37.1 | 64.8 + 17.35 | 98.03 + 33.51 | 88.84 + 3.69 |
| 22 | 119.67 + 19.05 | 75.12 + 20.05 | 117.02 + 42.1 | 105.66 + 5.49 |
| 26 | 130.97 + 20.61 | 81.53 + 26.16 | 131.58 + 23.41 | 124.55 + 7.90 |
| 29 | 170.99 + 51.67 | 114.65 + 34.57 | 164.90 + 37.18 | 182.15 + 14.79 |
| 32 | 191.0 + 48.36 | 129.06 + 32.08 | 191.68 + 45.65 | 196.66 + 18.65 |
| | \multicolumn{4}{c}{Tumour weight (g)} | | | |
| | .31 + .09 | .19 + .08 | .29 + .15 | .30 + .07 |

We claim:

1. A benzothiazole compound represented by the structural formula I below, or a pharmaceutically acceptable salt thereof,

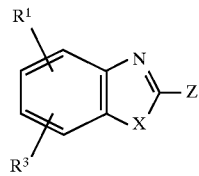

wherein

X is S;

$R^1$ and $R^3$ are each independently hydrogen, alkyl, hydroxyl, alkoxy or aralkoxy; and Z is a group represented by the structural formula II below

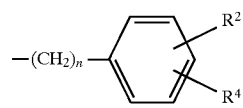

where n=0 or 1, $R^2$ is hydrogen, $NH_2$, $NO_2$, $N_3$, halogen or an alkyl or substituted alkyl oxysulphonyl group; and $R^4$ is hydrogen, $NO_2$, $N_3$, pyrrolidino, piperidino, morpholino or $NR^5R^6$ where $R^5$ and $R^6$ each represent hydrogen or alkyl;

with the proviso that if $R^4$ is hydrogen $R^2$ is selected from $NH_2$, $NO_2$ and $N_3$, and if one of $R^2$ and $R^4$ is hydrogen and the other is —$NH_2$ neither $R^1$ nor $R^3$ is 6-alkyl, and with the further proviso that if $R^1$ and $R^3$ are both hydrogen or if one of $R^1$ and $R^3$ is alkyl and the other is hydrogen, then $R^2$ is not chloro when $R^4$ is 4-$NH_2$ and is not hydrogen when $R^4$ is 4-$NH_2$, 3-$NH_2$, 3-$NO_2$ or $N_3$ and with the further proviso that alkyl groups when present as such in the compound or as a moiety in other groups such as alkoxy are each composed of less than 6 carbon atoms.

2. A compound as claimed in claim 1 wherein at least one of $R^2$ and $R^4$ is an amino or a substituted amino group.

3. A 2-arylbenzothiazole compound as claimed in claim 1 wherein Z is

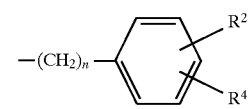

and $R^4$ is $NH_2$.

4. A compound as claimed in claim 3 wherein $R^2$ is 2-Cl.

5. A compound as claimed in claim 1 wherein $R^1$ is hydrogen and $R^3$ is alkoxy or benzyloxy.

6. A compound as claimed in claim 1 wherein at least one of the following features:

(a) at least some alkyl groups when present as such or as a moiety in other groups such as alkoxy are selected from methyl and ethyl;

(b) halo substituents, when present, are selected from fluorine and chlorine;

(c) $R^2$ is selected from hydrogen and 2-halogen, and $R^4$ is amino.

7. A compound as claimed in claim 1 said compound being a substituted 2-phenylbenzothiazole compound wherein the combination of substituents $R^1$, $R^2$, $R^3$, $R^4$ and X is selected from the following combinations:

| $R^1$ | $R^3$ | X | $R^2$ | $R^4$ |
|---|---|---|---|---|
| H | H | S | 2-$NH_2$ | 4-H |
| H | H | S | H | 4-$NMe_2$ |
| H | H | S | H | 4-$NEt_2$ |
| H | H | S | H | 4-Pyrrolidino |
| H | H | S | H | 4-Piperidino |
| H | H | S | H | 4-Morpholino |
| H | H | S | H | 4-$NO_2$ |
| H | H | S | 2-$NO_2$ | 4-H |
| H | H | S | 3-I | 4-$NH_2$ |
| H | H | S | 2-F | 4-$NH_2$ |
| H | H | S | 2-F | 4-$NO_2$ |
| H | H | S | 2-F | 4-$N_3$ |
| H | H | S | 2-Cl | 4-$NO_2$ |
| H | H | S | 2-Cl | 4-$N_3$ |
| 4-OMe | H | S | 2-Cl | 4-$NO_2$ |
| 5-OMe | H | S | 2-Cl | 4-$NO_2$ |
| 6-OMe | H | S | H | 4-$NO_2$ |
| 6-OMe | H | S | 2-Cl | 4-$NO_2$ |
| 7-OMe | H | S | 2-Cl | 4-$NO_2$ |
| 5-OBenzyl | H | S | 2-Cl | 4-$NO_2$ |
| 6-OBenzyl | H | S | 2-Cl | 4-$NO_2$ |
| 7-OBenzyl | H | S | 2-Cl | 4-$NO_2$ |
| 5-OMe | 6-OMe | S | H | 4-$NO_2$ |
| 6-OMe | 7-OMe | S | H | 4-$NO_2$ |
| 5-OMe | 7-OMe | S | H | 4-$NO_2$ |
| 4-OMe | H | S | 2-Cl | 4-$NH_2$ |
| 5-OMe | H | S | 2-Cl | 4-$NH_2$ |
| 6-OMe | H | S | 2-Cl | 4-$NH_2$ |

-continued

| R¹       | R³    | X | R²                      | R⁴     |
|----------|-------|---|-------------------------|--------|
| 5-OH     | H     | S | 2-Cl                    | 4-NH₂  |
| 6-OH     | H     | S | 2-Cl                    | 4-NH₂  |
| 5-OBenzyl| H     | S | 2-Cl                    | 4-NH₂  |
| H        | H     | S | 6-OSO₂CF₃               | 3-NH₂  |
| H        | H     | S | 3-OSO₂CF₃               | 4-NH₂  |
| 6-Me     | H     | S | 3-OSO₂CF₃               | 4-NH₂  |
| H        | H     | S | 5-OSO₂CF₃               | 2-NH₂  |
| 7-OBenzyl| H     | S | 2-Cl                    | 4-NH₂  |
| 6-OMe    | H     | S | H                       | 4-NH₂  |
| 6-OH     | H     | S | H                       | 4-NH₂  |
| 5-OMe    | 7-OMe | S | H                       | 4-NH₂  |
| 5-OH     | 7-OH  | S | H                       | 4-NH₂  |
| 5-OH     | 7-OMe | S | H                       | 4-NH₂  |
| 5-OMe    | 6-OMe | S | H                       | 4-NH₂  |

8. A compound selected from the group consisting of one of the following:

2-(4-Dimethylaminophenyl)benzothiazole
2-(4-Diethylaminophenyl)benzothiazole
2-(2-Aminophenyl)benzothiazole
2-(2-Fluorophenyl)benzothiazole
2-(4-Aminobenzyl)benzothiazole
2-(4-Pyridyl)benzothiazole
2-[4-(Pyrrolidin-1-yl)phenyl]benzothiazole
2-(2-Chloro-4-nitrophenyl)benzothiazole
6-Methoxy-2-(4-nitrophenyl)benzothiazole
2-(2-Chloro-4-nitrophenyl)-6-methoxybenzothiazole
2-(2-Chloro-4-nitrophenyl)-7-methoxybenzothiazole
2-(2-Chloro-4-nitrophenyl)-4-methoxybenzothiazole
2-(4-Amino-2-chlorophenyl)-4-methoxybenzothiazole
2-(4-Amino-2-chlorophenyl)-5-methoxybenzothiazole
2-(4-Amino-2-chlorophenyl)-6-methoxybenzothiazole
2-(4-Amino-2-chlorophenyl)-7-methoxybenzothiazole
2-[4-(Morpholin-4-yl)phenyl]benzothiazole
2-[4-(Piperidin-1-yl)phenyl]benzothiazole
Ethanesulphonic acid salt of 2-(4-aminophenyl)-benzothiazole or
2-(4-Aminophenyl)benzothiazole methanesulphonic acid salt.

9. A compound as claimed in claim 1 which is an acid addition salt derived from an acid selected from the group consisting of: hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

10. 2-(4-Amino-3-iodophenyl)benzothiazole or a pharmaceutically acceptable salt thereof.

11. A pharmaceutical composition comprising an effective amount of a benzothiazole compound of structural formula I below, or a pharmaceutically acceptable salt thereof,

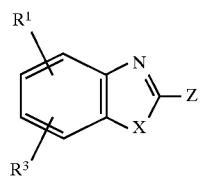

wherein
X is S;
R¹ and R³ are each independently hydrogen, alkyl, hydroxyl, alkoxy or aralkoxy; and
Z is a group represented by the structural formula II below

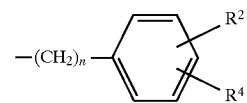

where n=0 or 1,
R² is hydrogen, NH₂, NO₂, N₃, halogen or an alkyl or substituted alkyl oxysulphonyl group; and
R⁴ is hydrogen, NO₂, N₃, pyrrolidino, piperidino, morpholino or NR⁵R⁶ where
R⁵ and R⁶ each represent hydrogen or alkyl;

with the proviso that when R⁴ is hydrogen R² is selected from NH₂, NO₂ and N₃, and when one of R² and R⁴ is hydrogen and the other is —NH₂ neither R¹ nor R³ is hydrogen or 6-alkyl, R² is not chloro when R⁴-NH₂ and is not hydrogen when R⁴ is 4-NH₂, 3-NH₂, 3-NO₂or N₃.

and with the further proviso that alkyl groups when present as such in the compound or as a moiety in other groups such as alkoxy are each composed of less than 6 carbon atoms, together with a pharmaceutically acceptable carrier.

12. A pharmaceutical composition as claimed in claim 11 wherein at least one of R² and R⁴ is an amino or a substituted amino group.

13. A pharmaceutical composition as claimed in claim 11 wherein Z in the benzothiazole compound is

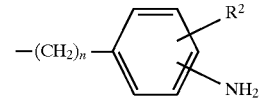

14. A pharmaceutical composition as claimed in claim 13 wherein R² is 2-Cl.

15. A pharmaceutical composition as claimed in claim 11 wherein R¹ is hydrogen and R³ is selected from alkoxy and benzyloxy.

16. A pharmaceutical composition as claimed in claim 11 wherein at least one of the following features:
 (a) at least some alkyl groups when present as such or as a moiety in other groups such as alkoxy are selected from methyl and ethyl;
 (b) halo substituents, when present, are selected from fluorine and chlorine;
 (c) R² is selected from hydrogen and 2-halogen, and R⁴ is amino.

17. A pharmaceutical composition as claimed in claim 13 wherein R² is 3-I.

18. A pharmaceutical composition as claimed in claim 11 wherein said benzothiazole compound is a substituted 2-phenylbenzothiazole compound.

19. A pharmaceutical composition as claimed in claim 11 wherein said benzothiazole compound is a substituted 2-phenylbenzothiazole compound wherein the combination of substituents R¹, R², R³, R⁴ and X is selected from the following combinations:

| R¹ | R³ | X | R²    | R⁴           |
|----|----|---|-------|--------------|
| H  | H  | S | 2-NH₂ | 4-H          |
| H  | H  | S | H     | 4-NMe₂       |
| H  | H  | S | H     | 4-NEt₂       |
| H  | H  | S | H     | 4-Pyrrolidino|
| H  | H  | S | H     | 4-Piperidino |
| H  | H  | S | H     | 4-Morpholino |

-continued

| R¹ | R³ | X | R² | R⁴ |
|---|---|---|---|---|
| H | H | S | H | 4-NO² |
| H | H | S | 2-NO₂ | 4-H |
| H | H | S | H | 4-N₃ |
| H | H | S | 3-N₃ | 4-H |
| H | H | S | 3-I | 4-NH₂ |
| H | H | S | 2-F | 4-NH₂ |
| H | H | S | 2-F | 4-NO₂ |
| H | H | S | 2-F | 4-N₃ |
| H | H | S | 2-Cl | 4-NO₂ |
| H | H | S | 2-Cl | 4-N₃ |
| 4-OMe | H | S | 2-Cl | 4-NO₂ |
| 5-OMe | H | S | 2-Cl | 4-NO₂ |
| 6-OMe | H | S | H | 4-NO₂ |
| 6-OMe | H | S | 2-Cl | 4-NO₂ |
| 7-OMe | H | S | 2-Cl | 4-NO₂ |
| 5-OBenzyl | H | S | 2-Cl | 4-NO₂ |
| 6-OBenzyl | H | S | 2-Cl | 4-NO₂ |
| 7-OBenzyl | H | S | 2-Cl | 4-NO₂ |
| 5-OMe | 6-OMe | S | H | 4-NO₂ |
| 6-OMe | 7-OMe | S | H | 4-NO₂ |
| 5-OMe | 7-OMe | S | H | 4-NO₂ |
| 4-OMe | H | S | 2-Cl | 4-NH₂ |
| 5-OMe | H | S | 2-Cl | 4-NH₂ |
| 6-OMe | H | S | 2-Cl | 4-NH₂ |
| 5-OH | H | S | 2-Cl | 4-NH₂ |
| 6-OH | H | S | 2-Cl | 4-NH₂ |
| 5-OBenzyl | H | S | 2-Cl | 4-NH₂ |
| H | H | S | 6-OSO₂CF₃ | 3-NH₂ |
| H | H | S | 3-OSO₂CF₃ | 4-NH₂ |
| 6-Me | H | S | 3-OSO₂CF₃ | 4-NH₂ |
| H | H | S | 5-OSO₂CF₃ | 2-NH₂ |
| 7-OBenzyl | H | S | 2-Cl | 4-NH2 |
| 6-OMe | H | S | H | 4-NH₂ |
| 6-OH | H | S | H | 4-NH₂ |
| 5-OMe | 7-OMe | S | H | 4-NH₂ |
| 5-OH | 7-OH | S | H | 4-NH₂ |
| 5-OH | 7-OMe | S | H | 4-NH₂ |
| 5-OMe | 6-OMe | S | H | 4-NH₂ |

20. A pharmaceutical composition comprising an effective amount of a benzothiazole compound selected from the group consisting of the following:
2-(4-Dimethylaminophenyl)benzothiazole
2-(4-Diethylaminophenyl)benzothiazole
2-(2-Aminophenyl)benzothiazole
2-(2-Fluorophenyl)benzothiazole
2-(4-Aminobenzyl)benzothiazole
2-(4-Pyridyl)benzothiazole
2-[4-(Pyrrolidin-1-yl)phenyl]benzothiazole
2-(3-Nitrophenyl)benzothiazole
2-(2-Chloro-4-nitrophenyl)benzothiazole
6-Methoxy-2-(4-nitrophenyl)benzothiazole
2-(2-Chloro-4-nitrophenyl)-6-methoxybenzothiazole
2-(2-Chloro-4-nitrophenyl)-7-methoxybenzothiazole
2-(2-Chloro-4-nitrophenyl)-4-methoxybenzothiazole
2-(4-Amino-2-chlorophenyl)benzothiazole
2-(4-Amino-2-chlorophenyl)-4-methoxybenzothiazole
2-(4-Amino-2-chlorophenyl)-5-methoxybenzothiazole
2-(4-Amino-2-chlorophenyl)-6-methoxybenzothiazole
2-(4-Amino-2-chlorophenyl)-7-methoxybenzothiazole
2-(4-Azidophenyl)benzothiazole
2-[4-(Morpholin-4-yl)phenyl]benzothiazole
2-[4-(Piperidin-1-yl)phenyl]benzothiazole
Ethanesulphonic acid salt of 2-(4-aminophenyl) benzothiazole
2-(4-Aminophenyl)benzothiazole methanesulphonic acid salt, together with a pharmaceutically acceptable carrier.

21. A pharmaceutical composition as claimed in claim 11 wherein said benzazole compound is in the form of an acid addition salt derived from an acid selected from the group comprising: hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

22. A pharmaceutical composition according to claim 11 in unit dosage form.

23. A method of treating a mammal suffering from breast cancer so as to inhibit or reduce growth or proliferation of breast cancer cells, said method comprising administering to said mammal an effective antitumour composition in the form of a pharmaceutical composition comprising an effective amount of a benzothiazole compound of structural formula I below or a pharmaceutically acceptable salt thereof

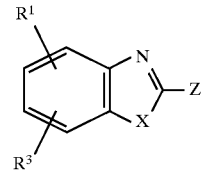

wherein
X is S;
R¹ and R³ are each independently hydrogen, alkyl, hydroxyl, alkoxy or aralkoxy; and
Z is a group represented by the structural formula II below

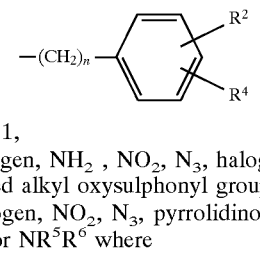

where n=0 or 1,
R² is hydrogen, NH₂, NO₂, N₃, halogen or an alkyl or substituted alkyl oxysulphonyl group: and
R⁴ is hydrogen, NO₂, N₃, pyrrolidino, piperidino, morpholino or NR⁵R⁶ where
R⁵ and R⁶ each represent hydrogen or alkyl:

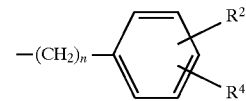

with the proviso that when R⁴ is hydrogen R² is selected from NH₂, NO₂, and N₃, and when one of R² and R⁴ is hydrogen and the other is —NH₂ neither R¹ nor R³ is 6-alkyl, and with the further proviso that alkyl groups when present as such in the compound or as a moiety in other groups such as alkoxy are each composed of less than 6 carbon atoms, together with a pharmaceutically acceptable carrier.

24. A pharmaceutical composition in unit dosage form suitable for administration comprising an effective amount of a benzothiazole compound of structural formula I below, or a pharmaceutically acceptable salt thereof,

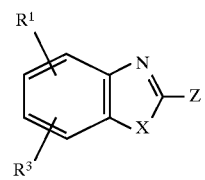

wherein
X is S;
R¹ and R³ are each independently hydrogen, alkyl, hydroxyl, alkoxy or aralkoxy; and Z is a group represented by the structural formula II below

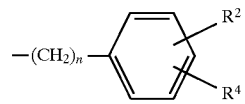

where n=0 or 1,
R² is hydrogen, NH₂, NO₂, N₃, halogen or an alklyl or substituted alkyl oxysulphonyl group; and
R⁴ is hydrogen, NO₂, N₃, pyrrolidino, piperidino, morpholino or NR⁵R⁶ where
R⁵ and R⁶ each represent hydrogen or alkyl;

with the proviso that when R⁴ is hydrogen R² is selected from NH₂, NO₂ and N₃, and when one of R² and R⁴ is hydrogen and the other is —NH₂ neither R¹ nor R³ is 6-alkyl, and with the further proviso that alkyl groups when present as such in the compound or as a moiety in other groups such as alkoxy are each composed of less than 6 carbon atoms, together with a pharmaceutically acceptable carrier.

* * * * *